United States Patent
Kimura

(10) Patent No.: US 10,916,007 B2
(45) Date of Patent: Feb. 9, 2021

(54) MAGNETIC RESONANCE IMAGING APPARATUS AND MAGNETIC RESONANCE IMAGING METHOD

(71) Applicant: TOSHIBA MEDICAL SYSTEMS CORPORATION, Otawara (JP)

(72) Inventor: Tokunori Kimura, Tochigi (JP)

(73) Assignee: TOSHIBA MEDICAL SYSTEMS CORPORATION, Tochigi (JP)

( * ) Notice: Subject to any disclaimer, the term of this patent is extended or adjusted under 35 U.S.C. 154(b) by 466 days.

(21) Appl. No.: 14/610,180

(22) Filed: Jan. 30, 2015

(65) Prior Publication Data

US 2015/0170364 A1 Jun. 18, 2015

Related U.S. Application Data

(63) Continuation of application No. PCT/JP2013/070517, filed on Jul. 29, 2013.

(30) Foreign Application Priority Data

Aug. 4, 2012 (JP) ................................ 2012-173500

(51) Int. Cl.
 *G06T 7/00* (2017.01)
 *G01R 33/56* (2006.01)
 (Continued)

(52) U.S. Cl.
 CPC ........ *G06T 7/0012* (2013.01); *G01R 33/5608* (2013.01); *G06K 9/46* (2013.01);
 (Continued)

(58) Field of Classification Search
 CPC ..................... G06T 5/00; G06T 7/0012; G06T 2207/10088; G06T 2207/10092;
 (Continued)

(56) References Cited

U.S. PATENT DOCUMENTS 5,341,099 A * 8/1994 Suzuki ................. G01R 33/561
 324/307
6,208,139 B1 * 3/2001 Foo ...................... G01R 33/561
 324/307
(Continued)

FOREIGN PATENT DOCUMENTS

| CN | 102415882 A | 4/2012 |
|---|---|---|
| JP | 6-022930 | 2/1994 |

(Continued)

OTHER PUBLICATIONS

Machine Translation of the Japaense office action cited in the IDS, dated Jul. 7, 2017.*

(Continued)

*Primary Examiner* — Vincent Rudolph
*Assistant Examiner* — Timothy Choi
(74) *Attorney, Agent, or Firm* — Nixon & Vanderhye, P.C.

(57) ABSTRACT

According to one embodiment, an MRI apparatus includes a data acquisition unit and an image generation unit. The data acquisition unit acquires MR data from an object. The MR data correspond to a sampling region asymmetric in a wave number direction in a k-space. The image generation unit generates amplitude image data, in a real space, based on first k-space data after zero padding to a non-sampling region of the MR data and generates MR image data by data processing of the amplitude image data or convolution processing of the amplitude image data. The data processing converts the amplitude image data into second k-space data, performs filtering of the second k-space data and converts the second k-space data after the filtering into real space data. The convolution processing uses a function in the real space. The function is derived by converting a window function for the filtering.

14 Claims, 9 Drawing Sheets

(51) Int. Cl.
*G06T 5/00* (2006.01)
*A61B 5/055* (2006.01)
*G06K 9/46* (2006.01)

(52) U.S. Cl.
CPC ............... *G06T 5/00* (2013.01); *A61B 5/055* (2013.01); *G06T 2207/10088* (2013.01)

(58) Field of Classification Search
CPC ........... G06T 2207/10096; G06T 2207/30004; G06K 9/46; G01R 33/5608
See application file for complete search history.

(56) References Cited

U.S. PATENT DOCUMENTS

| | | | | |
|---|---|---|---|---|
| 6,393,313 | B1* | 5/2002 | Foo | A61B 5/055 324/307 |
| 7,298,144 | B2* | 11/2007 | Reeder | G01R 33/4828 324/307 |
| 2008/0309334 | A1 | 12/2008 | Ikeda | |
| 2011/0098552 | A1* | 4/2011 | Takai | G01R 33/561 600/410 |
| 2012/0074940 | A1 | 3/2012 | Kimura | |
| 2012/0081116 | A1 | 4/2012 | Takai | |

FOREIGN PATENT DOCUMENTS

| | | | | |
|---|---|---|---|---|
| JP | 7-031605 | | 2/1995 | |
| JP | H07031605 | * | 3/1995 | ............. A61B 5/055 |
| JP | 9-238912 | | 9/1997 | |
| JP | 2006-149565 | | 6/2006 | |
| JP | 2008-307228 | | 12/2008 | |
| JP | 2012-070939 | | 4/2012 | |
| JP | 2012-090957 | | 5/2012 | |

OTHER PUBLICATIONS

"Google Translate", Japanese to English machine translation of relevant Figure 1 labels of the Hitoshi reference (JP H07-031605).*
Xu et al., "Partial Fourier Imaging in Multi-Dimensions: A Means to Save a Full Factor of Two in Time", Oct. 2001, Wiley-Liss, Journal of Magnetic Resonance Imaging, vol. 14, p. 628-635. (Year: 2001).*
Office Action dated May 26, 2015 in CN Patent Application No. 201380002760.X.
Notification of Transmittal of Translation of the International Preliminary Report on Patentability in PCT/JP2013/070517 dated Feb. 19, 2015.
International Search Report for PCT/JP2013/070517, dated Sep. 17, 2013.
Written Opinion of the International Searching Authority for PCT/JP2013/070517, dated Sep. 17, 2013.
G. McGibney et al. "Quantitative Evaluation of Several Partial Fourier Reconstruction Algorithms Used in MRI", Magn Reson Med. Jul. 1993, vol. 30, pp. 51-59.
First Japanese office action dated Jul. 4, 2017 in Patent Application No. JP 2013-157171.

* cited by examiner

MAGNETIC RESONANCE IMAGING APPARATUS AND MAGNETIC RESONANCE IMAGING METHOD

CROSS REFERENCES TO RELATED APPLICATIONS

This is a continuation of Application PCT/JP2013/70517, filed on Jul. 29, 2013.

This application is based upon and claims the benefit of priority from Japanese Patent Application No. 2012-173500, filed on Aug. 4, 2012; the entire contents of which are incorporated herein by reference.

FIELD

Embodiments described herein relate generally to an MRI (magnetic resonance imaging) apparatus and a magnetic resonance imaging method.

BACKGROUND

MRI is an imaging method which magnetically excites nuclear spin of an object set in a static magnetic field with a RF (radio frequency) signal having the Larmor frequency and reconstructs an image based on MR (magnetic resonance) signals generated due to the excitation.

The AFI (Asymmetric Fourier Imaging) method is known as one imaging method in MRI. The AFI method is a method for sampling data asymmetrically in the wavenumber direction in k-space and reconstructing image data after performing phase correction using phase distribution estimates based on the sampled data. According to the AFI method, image data similar to image data generated from data symmetrically sampled in k-space can be generated.

For the AFI method, various methods, such as the Margosian method, the FIR (finite impulse response) method, the MoFIR (Modified FIR) method, the POCS (projection on to convex sets) method and the hybrid method, are suggested. Moreover, a method for sampling data asymmetrically in k-space and performing Fourier Transformation (FT) after 0-filling of the part having no data is known although it is not included in the AFI method. In 0-filling, it is known that a remarkable blur occurs in an image when the degree in asymmetry property of k-space data is large.

In the Margosian method, real space (r-space) data corresponding to asymmetrically sampled k-space data are generated by performing a FT after applying a homodyne filter, which is a window function, with the asymmetric k-space data. On the other hand, a phase distribution is estimated based on the symmetrically sampled k-space data, in the low frequency region in the vicinity of the center of the k-space, among the asymmetrically sampled k-space data. Then, a phase correction of the real space data corresponding to the asymmetric k-space data is performed using the estimated phase distribution.

The POCS method is an improved method of the Margosian method, which performs POCS loop processing after the Margosian method. The POCS loop processing is processing which repeats real part extraction processing, composite processing, and phase correction processing, in order to make the imaginary parts of real space data converge so that changes in the imaginary parts become not more than a threshold value. By real part extraction processing, only real parts of the real space data after phase correction are left while imaginary parts become zero. By composite processing, the non-sampling part of k-space data obtained by the Inverse Fourier Transformation (IFT) after returning phases of the real space data subjected to the real part extraction are combined with the sampling part of the original data. The phase correction processing is performed to the real space data obtained by the FT of the k-space data after the composite processing. The POCS method is based on the principle that the imaginary parts of real space data become zero if the phase correction is perfect. According to the POCS method, the error in the phase correction, which occurs due to homodyne filter processing in the Margosian method, can be reduced by repeating the POCS loop processing several times.

On the other hand, in the FIR method, phase correction is performed before applying the homodyne filter with the asymmetrically sampled k-space data. That is, in the FIR method, real space data after phase correction are transformed into k-space data by IFT, after phase correction of the real space data generated by FT of the asymmetric k-space data. Then, the homodyne filter is applied with k-space data after phase correction. Although data processing time in the FIR method becomes longer, by the time corresponding to the two FTs, than the Margosian method, the error of the phase correction due to the homodyne filter processing can be reduced since phase correction is performed before homodyne filter processing.

The MoFIR method is an improved method of the FIR method by which the phase distribution used for the phase correction is estimated based on all the k-space data including not only the symmetrically sampled k-space data in the low frequency region but the asymmetrically sampled part. That is, the MoFIR method estimates the phase distribution used for the phase correction based on all the asymmetrically sampled k-space data while the FIR method estimates the phase distribution in the low frequency region for the phase correction, based on the k-space data only in the low frequency region in the vicinity of the center of the k-space. Accordingly, the MoFIR method can estimate the phase distribution in a higher frequency region compared with the FIR method though the estimated phase distribution differs from the real phase distribution. Therefore, the MoFIR method can reduce the error of the phase correction due to the homodyne filter processing in the Margosian method or the FIR method.

On the other hand, in the 0-filling which is the simplest reconstruction method of the asymmetric sampling data, blur occurs in an image. However, in case of asymmetric sampling with a comparatively small asymmetry degree with which 70% or more of all the data are sampled, blur of an image becomes in an acceptable range. Moreover, when the 0-filling is performed, special processing is unnecessary and artifacts due to phase overcorrection in the AFI do not appear. Therefore, the 0-filling is still often used when the degree of asymmetry is comparatively small.

The hybrid method is a method which combines the 0-filling with the AFI method. That is, the hybrid method is a method for combining a 0-fill image, obtained by the 0-filling, with an AFI image, obtained by the AFI, by a weighted addition. More specifically, the weights are adjusted so that a part having large phase differences or large amplitude differences between the 0-fill image and the AFI image becomes the 0-fill image while a part having small phase differences or small amplitude differences becomes the AFI image.

According to the AFI method as described above, shortening of an echo time (TE) is possible when the asymmetric direction of k-space data is a read-out direction of the k-space data. On the other hand, when the asymmetric direction of the k-space data is an encoding direction, an imaging time can be shortened. However, in the AFI method, both further shortening of an imaging time and improvement of an image quality are desired.

Accordingly, an object of the present invention is to provide a magnetic resonance imaging apparatus and a magnetic resonance imaging method which can generate image data, with a higher accuracy and a higher speed, based on MR data asymmetrically sampled in a k-space.

PRIOR TECHNICAL LITERATURE

[Patent literature 1] JPA 2012-070939

DETAILED DESCRIPTION

In general, according to one embodiment, a magnetic resonance imaging apparatus includes a data acquisition unit and an image generation unit. The data acquisition unit is configured to acquire magnetic resonance data from an object. The magnetic resonance data correspond to a sampling region asymmetric in a wave number direction in a k-space. The image generation unit is configured to generate amplitude image data, in a real space, based on first k-space data after zero padding to a non-sampling region of the magnetic resonance data and generate magnetic resonance image data by data processing of the amplitude image data or convolution processing of the amplitude image data. The data processing converts the amplitude image data into second k-space data, performs filtering of the second k-space data and converts the second k-space data after the filtering into real space data. The convolution processing uses a function in the real space. The function is derived by converting a window function for the filtering.

Further, according to another embodiment, a magnetic resonance imaging method includes: acquiring magnetic resonance data from an object; and generating amplitude image data, in a real space, based on first k-space data after zero padding to a non-sampling region of the magnetic resonance data and generate magnetic resonance image data by data processing of the amplitude image data or convolution processing of the amplitude image data. The magnetic resonance data correspond to a sampling region asymmetric in a wave number direction in a k-space. The data processing converts the amplitude image data into second k-space data, performs filtering of the second k-space data and converts the second k-space data after the filtering into real space data. The convolution processing uses a function in the real space. The function is derived by converting a window function for the filtering.

A magnetic resonance imaging apparatus and a magnetic resonance imaging method according to embodiments of the present invention will be described with reference to the accompanying drawings.

Figure 1:
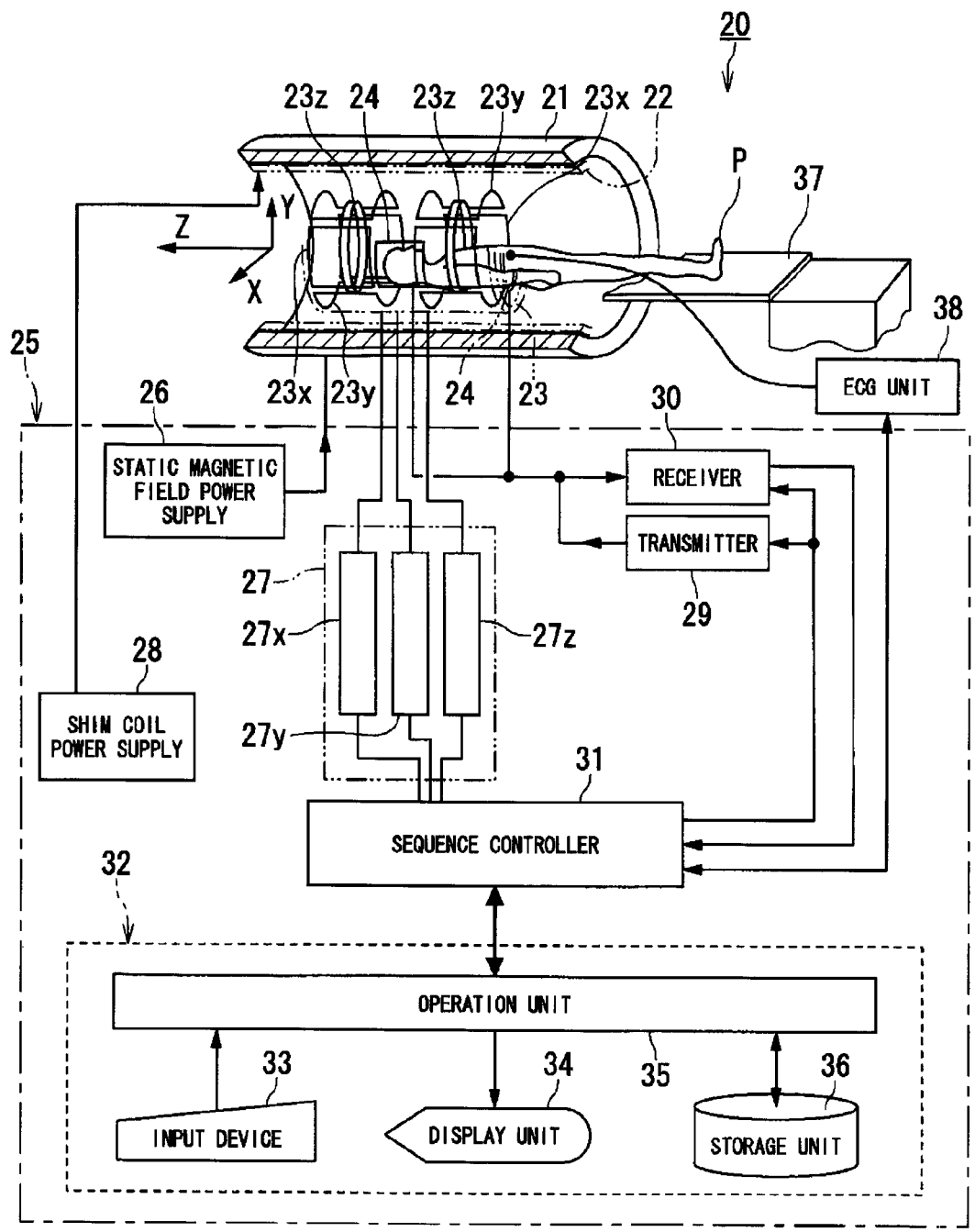
FIG. 1 is a block diagram showing a magnetic resonance imaging apparatus according to an embodiment of the present invention.

FIG. 1 is a block diagram showing a magnetic resonance imaging apparatus according to an embodiment of the present invention.

A magnetic resonance imaging apparatus 20 includes a static field magnet 21 for generating a static magnetic field, a shim coil 22 arranged inside the static field magnet 21 which is cylinder-shaped, a gradient coil 23 and RF coils 24.

The magnetic resonance imaging apparatus 20 also includes a control system 25. The control system 25 includes a static magnetic field power supply 26, a gradient power supply 27, a shim coil power supply 28, a transmitter 29, a receiver 30, a sequence controller 31 and a computer 32. The gradient power supply 27 of the control system 25 includes an X-axis gradient power supply 27x, a Y-axis gradient power supply 27y and a Z-axis gradient power supply 27z. The computer 32 includes an input device 33, a display unit 34, an operation unit 35 and a storage unit 36.

The static field magnet 21 communicates with the static magnetic field power supply 26. The static magnetic field power supply 26 supplies electric current to the static field magnet 21 to get the function to generate a static magnetic field in an imaging region. The static field magnet 21 includes a superconductivity coil in many cases. The static field magnet 21 gets current from the static magnetic field power supply 26 which communicates with the static field magnet 21 at excitation. However, once excitation has been made, the static field magnet 21 is usually isolated from the static magnetic field power supply 26. The static field magnet 21 may include a permanent magnet which makes the static magnetic field power supply 26 unnecessary.

The static field magnet 21 has the cylinder-shaped shim coil 22 coaxially inside itself. The shim coil 22 communicates with the shim coil power supply 28. The shim coil power supply 28 supplies current to the shim coil 22 so that the static magnetic field becomes uniform.

The gradient coil 23 includes an X-axis gradient coil 23x, a Y-axis gradient coil 23y and a Z-axis gradient coil 23z. Each of the X-axis gradient coil 23x, the Y-axis gradient coil 23y and the Z-axis gradient coil 23z which is cylinder-shaped is arranged inside the static field magnet 21. The gradient coil 23 has also a bed 37 in the area formed inside it which is an imaging area. The bed 37 supports an object P. The RF coils 24 include a whole body coil (WBC: whole body coil), which is built in the gantry, for transmission and reception of RF signals and local coils, which are arranged around the bed 37 or the object P, for reception of RF signals.

The gradient coil 23 communicates with the gradient power supply 27. The X-axis gradient coil 23x, the Y-axis gradient coil 23y and the Z-axis gradient coil 23z of the gradient coil 23 communicate with the X-axis gradient power supply 27x, the Y-axis gradient power supply 27y and the Z-axis gradient power supply 27z of the gradient power supply 27 respectively.

The X-axis gradient power supply 27x, the Y-axis gradient power supply 27y and the Z-axis gradient power supply 27z supply currents to the X-axis gradient coil 23x, the Y-axis gradient coil 23y and the Z-axis gradient coil 23z respectively so as to generate gradient magnetic fields Gx, Gy and Gz in the X, Y and Z directions in the imaging area.

The RF coils 24 communicate with transmitter 29 and/or receiver 30. The transmission RF coil 24 has a function to transmit an RF signal from transmitter 29 to object P. The reception RF coil 24 has a function to receive MR signals, generated due to nuclear spins inside the object P which are excited by the RF signal, which are input to receiver 30.

The sequence controller 31 of the control system 25 communicates with the gradient power supply 27, the transmitter 29 and the receiver 30. The sequence controller 31 has a function to storage sequence information describing control information needed in order to make the gradient power supply 27, the transmitter 29 and the receiver 30 drive and generate gradient magnetic fields Gx, Gy and Gz in the X, Y and Z directions and a RF signal by driving the gradient power supply 27, the transmitter 29 and the receiver 30 according to a predetermined sequence stored. The control information above-described includes motion control information, such as intensity, impression period and impression timing of the pulse electric current which should be applied to the gradient power supply 27

The sequence controller 31 is also configured to give raw data to the computer 32. The raw data is complex data obtained through the detection of a MR signal and A/D (analog to digital) conversion to the MR signal detected in the receiver 30.

The transmitter 29 has a function to give a RF signal to the RF coil 24 in accordance with control information provided from the sequence controller 31. The receiver 30 has a function to generate raw data which is digitized complex number data by detecting a MR signal given from the RF coil 24 and performing predetermined signal processing and A/D converting to the MR signal detected. The receiver 30 also has a function to give the generated raw data to the sequence controller 31.

In addition, an ECG (electro cardiogram) unit 38 for acquiring an ECG signal of the object P is provided with the magnetic resonance imaging apparatus 20. The ECG signal detected by the ECG unit 38 is output to the computer 32 through the sequence controller 31. Note that, a PPG (peripheral pulse gating) signal representing a beat as pulse wave information may be acquired instead of an ECG signal representing a beat as heart rate information.

The computer 32 gets various functions by the operation unit 35 executing some programs stored in the storage unit 36 of the computer 32. Alternatively, some specific circuits having various functions may be provided with the magnetic resonance imaging apparatus 20 instead of using some of the programs.

Figure 2:
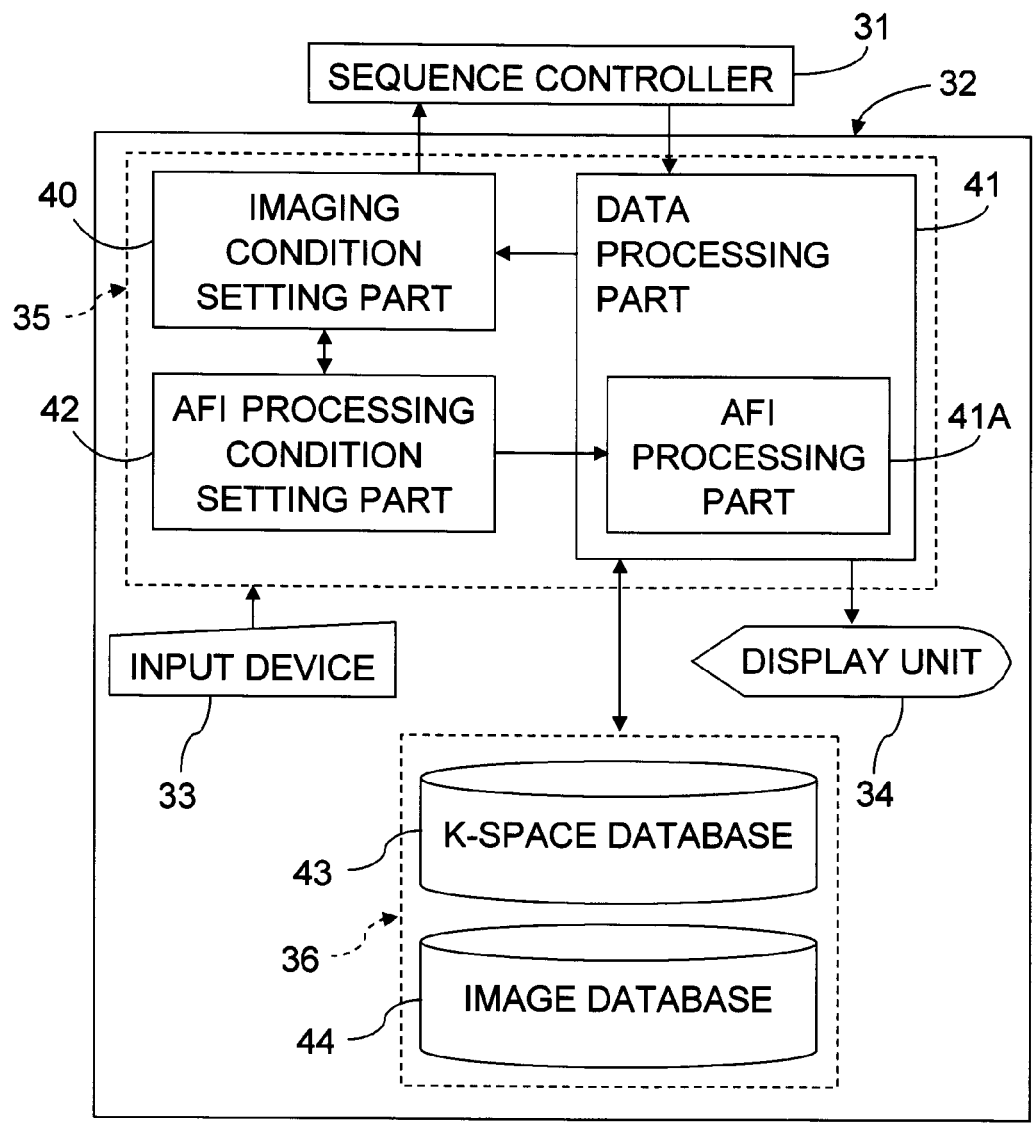
FIG. 2 is a functional block diagram of the computer shown in FIG. 1.

FIG. 2 is a functional block diagram of the computer 32 shown in FIG. 1.

The operation unit 35 of the computer 32 functions as an imaging condition setting part 40, a data processing part 41 and an AFI processing condition setting part 42 by executing the programs stored in the storage unit 36. Moreover, the storage unit 36 functions as a k-space database 43 and an image database 44. The data processing part 41 includes an AFI processing part 41A.

The imaging condition setting part 40 has a function to set imaging conditions including a pulse sequence based on direction information from the input device 33 and output the set imaging conditions to the sequence controller 31 to control a drive of the sequence controller 31.

Especially, the imaging condition setting part 40 is configured to set imaging conditions for AFI which acquires MR data, corresponding to a sampling region asymmetric in the wavenumber direction in a k-space, from an object P. The AFI method is an image reconstruction technique which approximately generates image data near image data based on symmetrically sampled MR data, using MR data sampled asymmetrically in the wave number direction in at least one axis direction of a two dimensional (2D) or three dimensional (3D) k-space. The AFI can be applied to various imaging including magnetic resonance angiography (MRA) and diffusion weighted imaging (DWI).

In case of 2D sampling, imaging conditions for AFI include a sampling region ($-K_c \leq k \leq K_{max}$) in a wave number direction in one direction k of a readout direction and a phase encode direction of k-space data. The boundary $K_c$ of the sampling region can be set variably according to the setting information from the AFI processing condition setting part 42, for example. The non-sampling region may be either a positive or a negative side in the k direction. Moreover, a sampling region and a non-sampling region may also be set as 3D regions. Here, an example case where a sampling region and a non-sampling region are set as 2D regions and the non-sampling region is the negative side will be explained.

The data processing part 41 has a function to receive raw data, acquired under conditions for AFI, from the sequence controller 31 to arrange the raw data as k-space data in the k-space formed in the k-space database 43 and a function to generate image data by image reconstruction processing including FT of the k-space data. Moreover, real space data, such as image data for a diagnosis and intermediate image data, may also be stored in the image database 44, as needed.

Therefore, k-space data is stored in the k-space database 43 while real space data is stored in the image database 44.

The AFI processing part 41A of the data processing part 41 has a function to perform AFI processing which generates image data, nearly similar to image data generated from symmetrically sampled k-space data, without phase correction processing, based on k-space data sampled asymmetrically in the wave number direction in a k-space. That is, the AFI processing part 41A is configured to perform the AFI processing without the phase correction processing, unlike the conventional AFI processing accompanied by the phase correction processing.

The AFI processing can be performed in order of generating the first k-space data by the 0-filling to the non-sampling region of MR data acquired from an asymmetric sampling region, generating amplitude image data by the FT of the first k-space data, transforming the amplitude image data into the second k-space data by the IFT of the amplitude image data, filtering of the second k-space data and generating image data by the FT of the second k-space data after the filtering. Therefore, the AFI processing part 41A is configured to generate the amplitude image data, in the real space, based on the first k-space data after the 0-filling to the non-sampling region of the MR data and generate MR image data by data processing by which the amplitude image data are transformed to the second k-space data, the second k-space data are subjected to the filtering and the second k-space data after the filtering are transformed to real space data.

Figure 3:
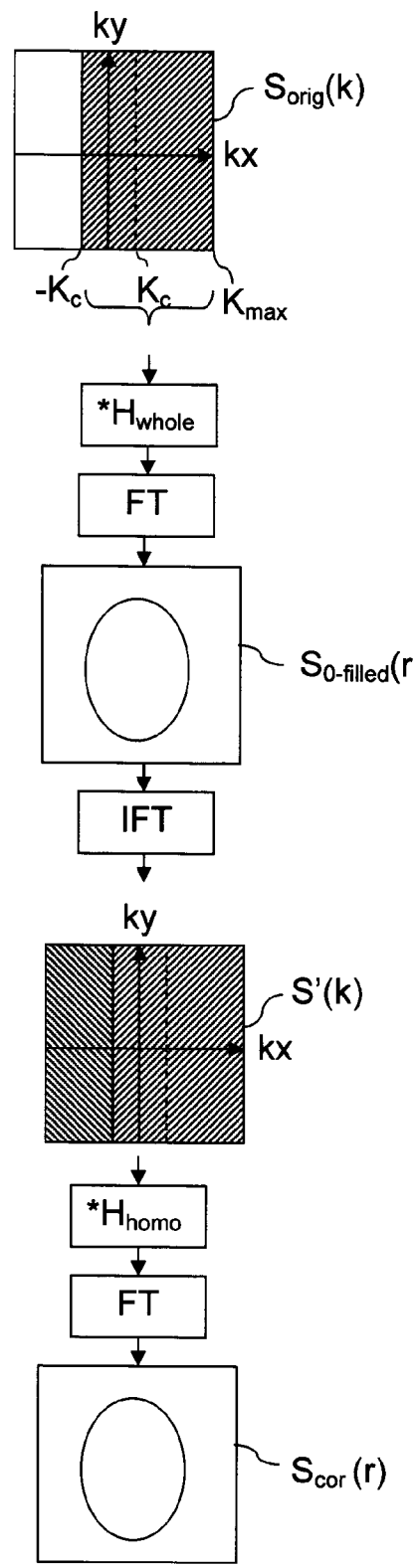
FIG. 3 is a chart explaining a method of AFI processing including filtering in the k-space performed in the AFI processing part shown in FIG. 2.

FIG. 3 is a chart explaining a method of AFI processing including filtering in the k-space performed in the AFI processing part 41A shown in FIG. 2.

When MR data are acquired according to imaging conditions under the AFI method in which the non-sampling region lies the negative side of a 2D k-space, MR data $S_{orig}(k)$ asymmetric in the wave number direction in the k-space are acquired. When the asymmetric direction is the kx direction in the k-space as shown in FIG. 3, the MR data $S_{orig}(k)$ are a data group whose parameter is a frequency k satisfying $-K_c \leq k \leq K_{max}$. Note that, $K_c$ is a cutoff frequency, of the non-sampling region, having a positive value and $K_{max}$ is the maximum frequency of the sampling region. Therefore, the relation of $0 < K_c < K_{max}$ is satisfied.

Next, the 0-filling to the non-sampling region of the asymmetric MR data $S_{orig}(k)$ is performed. The 0-filling can be performed by multiplying the window function $H_{whole}(k)$ defined by the formula (1) with the asymmetric MR data $S_{orig}(k)$.

$$H_{whole}(k) = H_{low}(k): -K_{max} \leq k \leq 0 \quad (1)$$
$$= 1: 0 < k \leq K_{max}$$

The function $H_{low}(k)$ in the formula (1) is a window function which extracts the symmetrical portion in the low frequency region from the asymmetric MR data $S_{orig}(k)$. In case of defining the window function, which extracts a low frequency region, using Gaussian, the window function can be expressed as the formula (2).

$$H_{low}(k) = 1: |k| \leq K_c - K_1 \quad (2)$$
$$= \exp[(-\ln 2)\{k - (Kc - K_1))/K_2\}^2]: K_c - K_1 < |k| \leq K_{max}$$

$K_1$ and $K_2$ in the formula (2) are constants for smoothly changing the low frequency region to be extracted.

Figure 4:
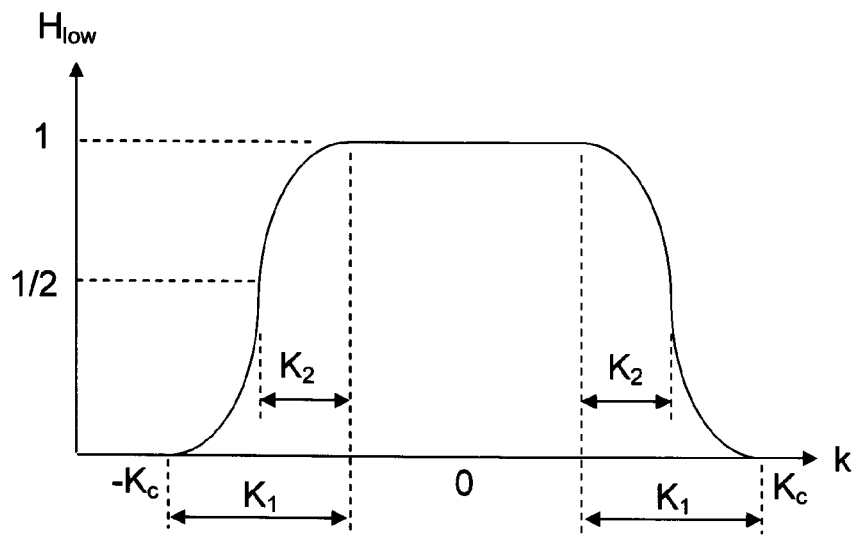
FIG. 4 shows a graph indicating the definition of the constants $K_1$ and $K_2$ in the window function $H_{low}(k)$ shown by the formula (2)

FIG. 4 shows a graph indicating the definition of the constants $K_1$ and $K_2$ in the window function $H_{low}(k)$ shown by the formula (2).

In FIG. 4, the horizontal axis represents the frequency k in the k-space while the vertical axis represents a gain of the window function $H_{low}(k)$. As shown in FIG. 4, the constant $K_1$ can be defined as a width of frequency in which the gain of the window function $H_{low}(k)$ is smoothly changed from the maximum value 1 to zero while the constant $K_2$ can be defined as a width of frequency in which the gain of the window function $H_{low}(k)$ is smoothly changed from the maximum value 1 to ½.

Figure 5:
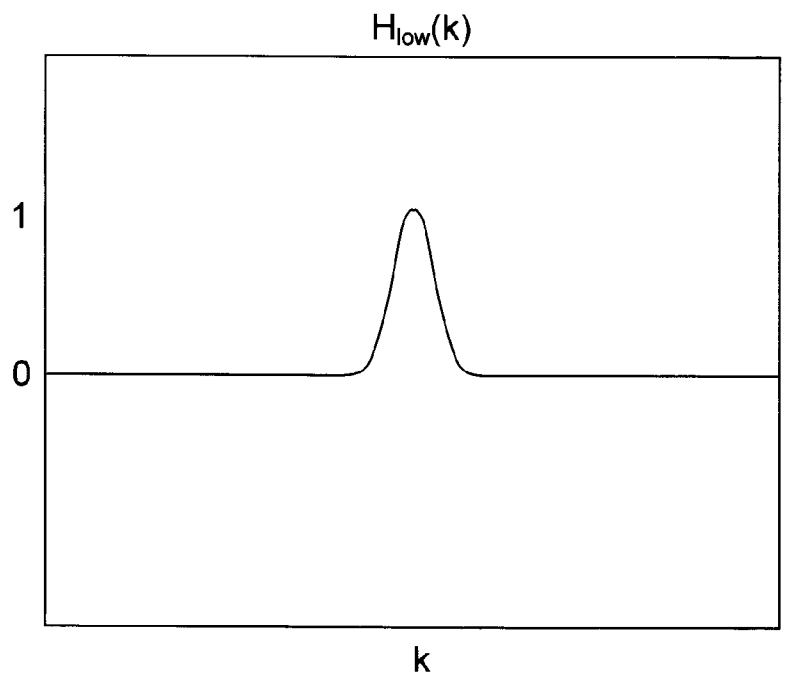
FIG. 5 is a graph showing an example of the window function $H_{low}(k)$ for the extraction of the low frequency region shown by the formula (2)
Figure 6:
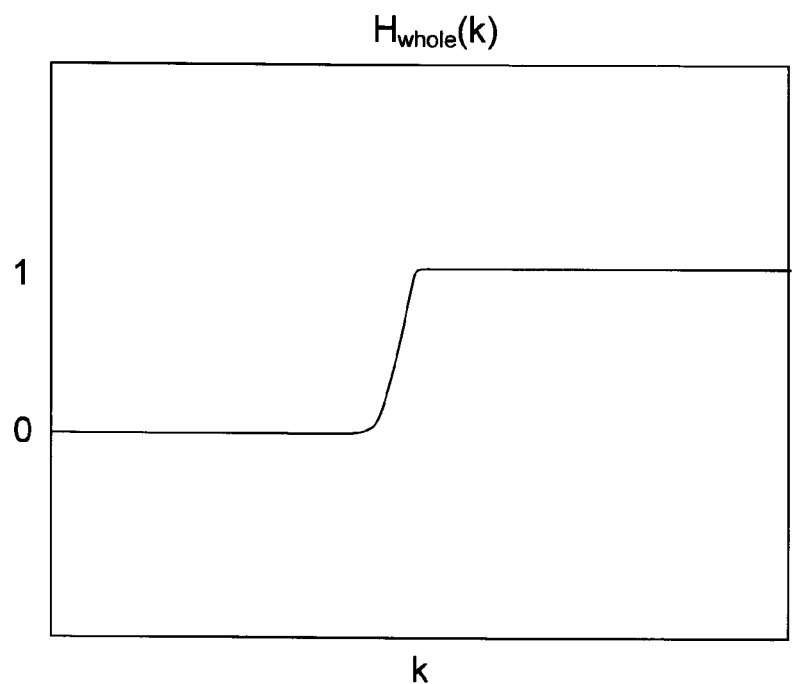
FIG. 6 is a graph showing an example of the window function $H_{whole}(k)$ for the 0-filling shown by the formula.

FIG. 5 is a graph showing an example of the window function $H_{low}(k)$ for the extraction of the low frequency region shown by the formula (2) while FIG. 6 is a graph showing an example of the window function $H_{whole}(k)$ for the 0-filling shown by the formula (1).

The respective horizontal axes of FIG. 5 and FIG. 6 represent the frequency k in the k-space while the respective vertical axes represent the gains of the window functions $H_{low}(k)$ and $H_{whole}(k)$. The 0-filling of the asymmetric MR data $S_{orig}(k)$ can be performed using the window function $H_{low}(k)$, for the extraction of the low frequency region, and the window function $H_{whole}(k)$, for the 0-filling, as illustrated in FIG. 5 and FIG. 6 respectively.

When the 0-filling of the asymmetric MR data $S_{orig}(k)$ has been completed, the first k-space data $S_{orig}(k)*H_{whole}(k)$ are generated. Next, the first k-space data $S_{orig}(k)*H_{whole}(k)$ after the 0-filling are subjected to the FT. Thereby, amplitude image data $S_{0\text{-}filled}(r)$ are generated as real space data. Next, the second k-space data S'(k) are generated by the IFT of the amplitude image data $S_{0\text{-}filled}(r)$ after the 0-filling.

The phase components of the amplitude image data $S_{0\text{-}filled}(r)$ after the 0-filling are zero. That is, the amplitude image data $S_{0\text{-}filled}(r)$ have values only in the real parts and the imaginary parts are zero. On the other hand, in the MoFIR method which is one of the conventional AFI methods, the phase correction of the real space data is performed using all the phase data. Consequently, the phase components of the real space data after the phase correction also become zero.

Therefore, it is considered that the distribution of the second k-space data S'(k) corresponding to the amplitude image data $S_{0\text{-}filled}(r)$ after the 0-filling becomes similar to the distribution of the k-space data after the phase correction in the MoFIR method. Accordingly, the second k-space data S'(k) corresponding to the amplitude image data $S_{0\text{-}filled}(r)$ after the 0-filling can be treated as the k-space data after the phase correction in the MoFIR method.

However, in the MoFIR method, the homodyne-high-pass filter is applied after phase correction, in order to correct the degradation in the high frequency components. The homodyne-high-pass filter is a window function, having an asymmetric gain, for the AFI processing. Specifically, the homodyne-high-pass filter is a filter whose gain to the non-sampling region is zero, gain to a symmetric part out of the sampling region is 1 time and gain to the sampling part having the sign opposite to that of the non-sampling region is twice. Normally, the gain of the homodyne-high-pass filter is determined so as to vary smoothly.

Therefore, the deterioration in the high frequency components, i.e., blur can be reduced by performing filter processing, equivalent to the homodyne-high-pass filter, of the second k-space data S'(k) corresponding to the amplitude image data $S_{0\text{-}filled}(r)$ after the 0-filling. This makes possible to generate MR image data having an image quality similar to that of the MR image data generated by the MoFIR method.

The filtering processing of the second k-space data S'(k) can be performed by multiplying a window function $H_{homo}$ with the second k-space data S'(k). As the window function $H_{homo}$, an asymmetric function or a symmetric function is presumable.

The characteristic of the second k-space data S'(k) obtained by the IFT of the amplitude image data $S_{0\text{-}filled}(r)$ includes the complex conjugate. That is, each real part of the second k-space data S'(k) is an even function while each imaginary part is an odd function. Therefore, the same result is obtained whether an asymmetric function is used or a symmetric function is used as the window function $H_{homo}$.

The non-sampling region of the second k-space data S'(k) also has data of which each intensity is one half of that in the case of full sampling. On the other hand, each intensity of the data in the sampling part of which sign is opposite to that of the non-sampling region is also one half of that in the case of full sampling.

Therefore, it is appropriate that the window function $H_{homo}$, for correcting the blur, used for the filter processing of the second k-space data S'(k) is a function which corrects each signal intensity of the second k-space data S'(k) into that in the case of full sampling. Consequently, it becomes possible to reduce the blur due to the 0-filling with suppressing the artifacts by the error corresponding to the error due to the phase correction.

Figure 7:
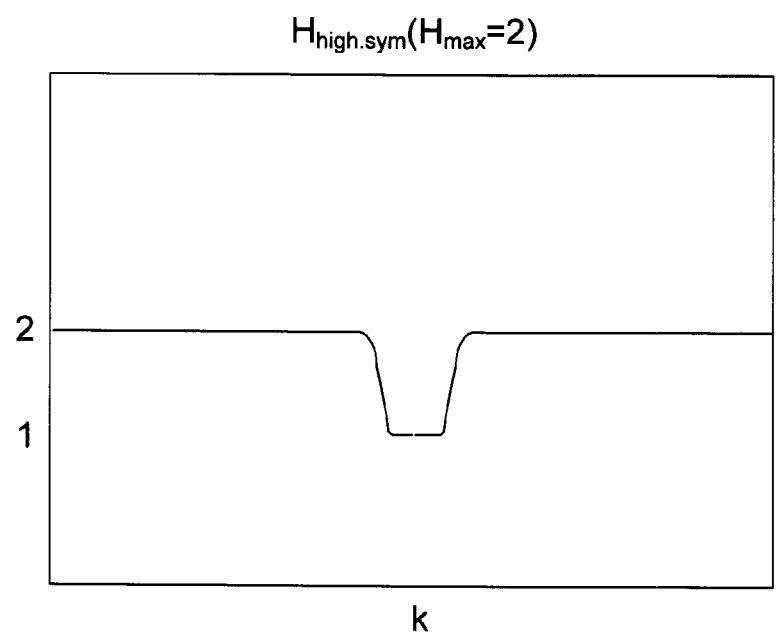
FIG. 7 is a graph showing an example of the symmetrical window function $H_{homo}$.

FIG. 7 is a graph showing an example of the symmetrical window function $H_{homo}$.

In FIG. 7, the horizontal axis represents the frequency k in the k-space while the vertical axis represents a gain of the window function $H_{homo}(k)$. As shown in FIG. 7, the filtering of the second k-space data S'(k) can be performed using the window function $H_{homo}(k)$ whose gain is set to be larger in the high frequency regions, consisting of the asymmetric sampling portion out of the asymmetric sampling region and the non-sampling region, than in the low frequency region consisting of the symmetric sampling portion out of the asymmetric sampling region. That is, the degradation in the high frequency component in the second k-space data S'(k) can be corrected by multiplying the window function $H_{homo}(k)$, symmetric with regard to the center of the k-space, with the second k-space data S'(k).

In case of using a window function $H_{homo}(k)$ axisymmetric with regard to the center of the k-space, it is appropriate to set the gain in the high frequency region not more than twice the gain in the low frequency region in view of the above-mentioned reason. In the example shown in FIG. 7, the maximum value $H_{max}$ of the gain of the window function $H_{homo}(k)$ corresponding to the high frequency region has been set to 2 which is the theoretical ideal value while the gain corresponding to the low frequency region has been set to 1.

When the axisymmetric window function $H_{homo}(k)$ is expressed by $H_{high.sym}(k)$, the axisymmetric window function $H_{high.sym}(k)$ can be calculated by the formula (3).

$$H_{high.sym}(k)=H_{low}(k):|k|\leq K_c=H_{max}-(H_{max}-1)*H_{low}(k): K_c<|k|\leq K_{max} \quad (3)$$

wherein $1<H_{max}\leq 2$. The function $H_{low}(k)$ in the formula (3) is the window function $H_{low}(k)$ for the extraction of the low frequency region defined by the formula (2). Therefore, the axisymmetric window function $H_{high.sym}(k)$ is to be a function whose changing portions of the gain before and after $k=\pm k_c$ change smoothly with the Gauss function. Thus, using a smoothly changing function as the symmetric or asymmetric window function $H_{homo}(k)$ makes it possible to correct the second k-space data S'(k) into continuous k-space data.

Figure 8:
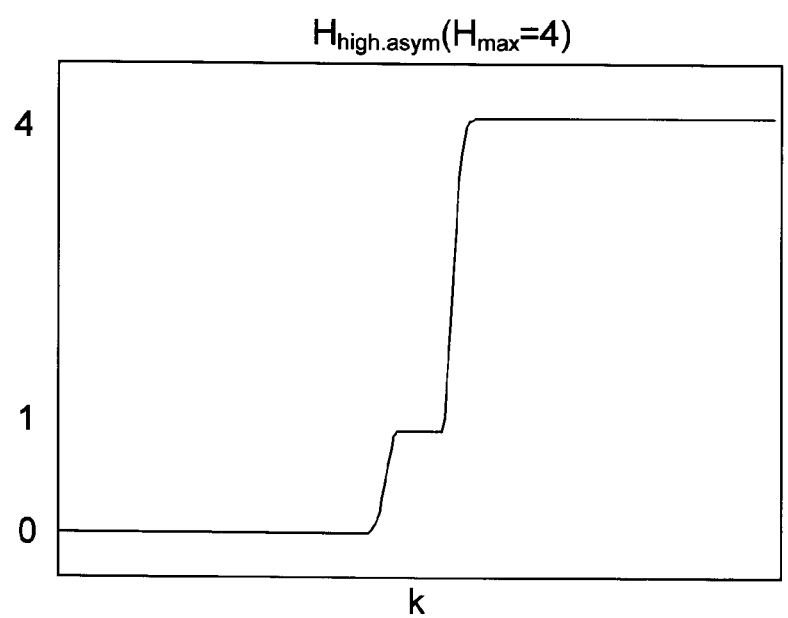
FIG. 8 is a graph showing an example of the asymmetric window function $H_{homo}$.

FIG. 8 is a graph showing an example of the asymmetric window function $H_{homo}$.

In FIG. 8, the horizontal axis represents the frequency k in the k-space while the vertical axis represents a gain of the window function $H_{homo}(k)$. As shown in FIG. 8, the filtering of the second k-space data S'(k) can be performed using the window function $H_{homo}(k)$ whose gain is set to be larger in the high frequency regions, consisting of the asymmetric sampling portion out of the asymmetric sampling region, than in the low frequency region consisting of the symmetric sampling portion out of the asymmetric sampling region. That is, the degradation in the high frequency component in the second k-space data S'(k) can be corrected by multiplying the window function $H_{homo}(k)$, asymmetric with regard to the center of the k-space, with the second k-space data S'(k).

In case of using a window function $H_{homo}(k)$ asymmetric with regard to the center of the k-space, it is appropriate to set the gain in the sampling portion in the high frequency side to be not less than twice and not more than four times the gain in the sampling portion in the low frequency side and to set the gain in the non-sampling region as zero in view of the above-mentioned reason. In the example shown in FIG. 8, the maximum value $H_{max}$ of the gain in the sampling portion in the high frequency side has been set to 4 which is the theoretical ideal value, the gain in the sampling portion in the low frequency side has been set to 1, and the gain in the non-sampling region has been set to zero, respectively.

When the asymmetric window function $H_{homo}(k)$ is expressed by $H_{high.asym}(k)$, the asymmetric window function $H_{high.asym}(k)$ can be calculated by the formula (4).

$$H_{high.asym}(k)=H_{low}(k):-K_{max}\leq k\leq 0=H_{max}-(H_{max}-1) *H_{low}(k): 0<k\leq k_{max} \quad (4)$$

wherein $2\leq H_{max}\leq 4$. Moreover, the window function $H_{low}(k)$ for the extraction of the low frequency region defined by the formula (2) is also used in the formula (4). Therefore, the asymmetric window function $H_{high.asym}(k)$ also changes smoothly by the Gauss function. Note that, the asymmetric window function $H_{high.asym}(k)$ shown in FIG. 8 and by the formula (4) is one in the case where the non-sampling region is in the negative side of the k-space. Therefore, in the case where the non-sampling region is in the positive side of the k-space, the polarity is inverted.

When the correction of the high frequency components of the second k-space data S'(k) using a symmetric or an asymmetric window function $H_{homo}(k)$ has been completed, MR image data $S_{cor}(r)$ can be generated as real space data by the FT. The MR image data $S_{cor}(r)$ generated here become image data having an image quality equivalent to that of the MR image data which have been subjected to the phase correction and the correction of the high frequency components in the conventional MoFIR method. The MR image data $S_{cor}(r)$ can be expressed as the formula (5-1) or the formula (5-2).

$$S_{cor}(r)=FT\{S(k)*H_{high.sym}(k)\} \quad (5-1)$$

$$S_{cor}(r)=FT\{S(k)*H_{high.asym}(k)\} \quad (5-2)$$

Note that, the AFI processing without the phase correction can be achieved also by performing the convolution processing, in the real space, of the amplitude image data $S_{0-filled}(r)$. In that case, the convolution processing is equivalent to the data processing which converts the amplitude image data $S_{0-filled}(r)$ into the second k-space data S'(k), performs the filtering of the second k-space data S'(k), and subsequently converts the second k-space data S'(k) into real space data. That is, the AFI processing can also be performed not in the k-space but in the real space.

Figure 9:
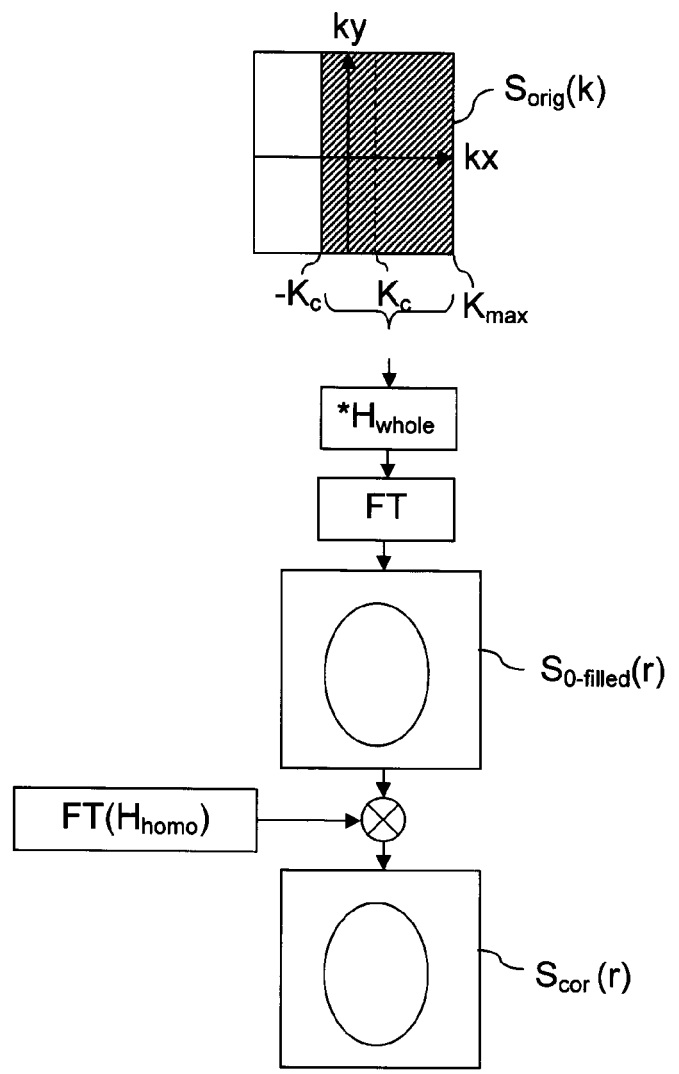
FIG. 9 is a chart explaining a method of AFI processing including convolution processing in the real space performed in the AFI processing part shown in FIG. 2.

FIG. 9 is a chart explaining a method of AFI processing including convolution processing in the real space performed in the AFI processing part 41A shown in FIG. 2. In FIG. 9, explanation about processing similar to processing shown in FIG. 3 is omitted.

When the convolution processing is performed in the real space, what is necessary is to perform the convolution processing of the amplitude image data $S_{0-filled}(r)$ using a function in the real space obtained by the FT of the symmetric or asymmetric window function $H_{homo}(k)$ for the filtering in the k-space, as shown in FIG. 9. That is, the convolution processing can be performed using a function in the real space equivalent to the window function $H_{homo}(k)$ for the k-space.

Note that, the filter function $FT(H_{homo})$ in the real space becomes an analytical formula. Accordingly, the filter function $FT(H_{homo})$ in the real space can be previously made into a table by a discretization and the FT of the window function $H_{homo}(k)$ for the k-space. Thereby, the calculation of the filter function $FT(H_{homo})$ in the real space can become unnecessary. That is, the filter function $FT(H_{homo})$ can be obtained by referring to the table.

The calculation of MR image data $S_{cor}(r)$ by the convolution processing using the filter function $FT(H_{homo})$ in the real space can be performed by the formula (6-1) or the formula (6-2).

$$S_{cor}(r)=\text{Convolve}\{S'(r), H_{high.sym}(r)\}=\text{Convolve}[S'(r), FT\{H_{high.sym}(k)\}] \quad (6\text{-}1)$$

$$S_{cor}(r)=\text{Convolve}\{S'(r), H_{high.asym}(r)\}=\text{Convolve}[S'(r), FT\{H_{high.asym}(k)\}] \quad (6\text{-}2)$$

wherein the Convolve in the formula (6-1) and the formula (6-2) expresses the operator of the convolution processing between the functions in { }.

Furthermore, loop processing which reduces the phase error remaining in the MR image data $S_{cor}(r)$ generated by the processing shown in FIG. 3 or FIG. 9 may also be performed as additional post processing.

Figure 10:
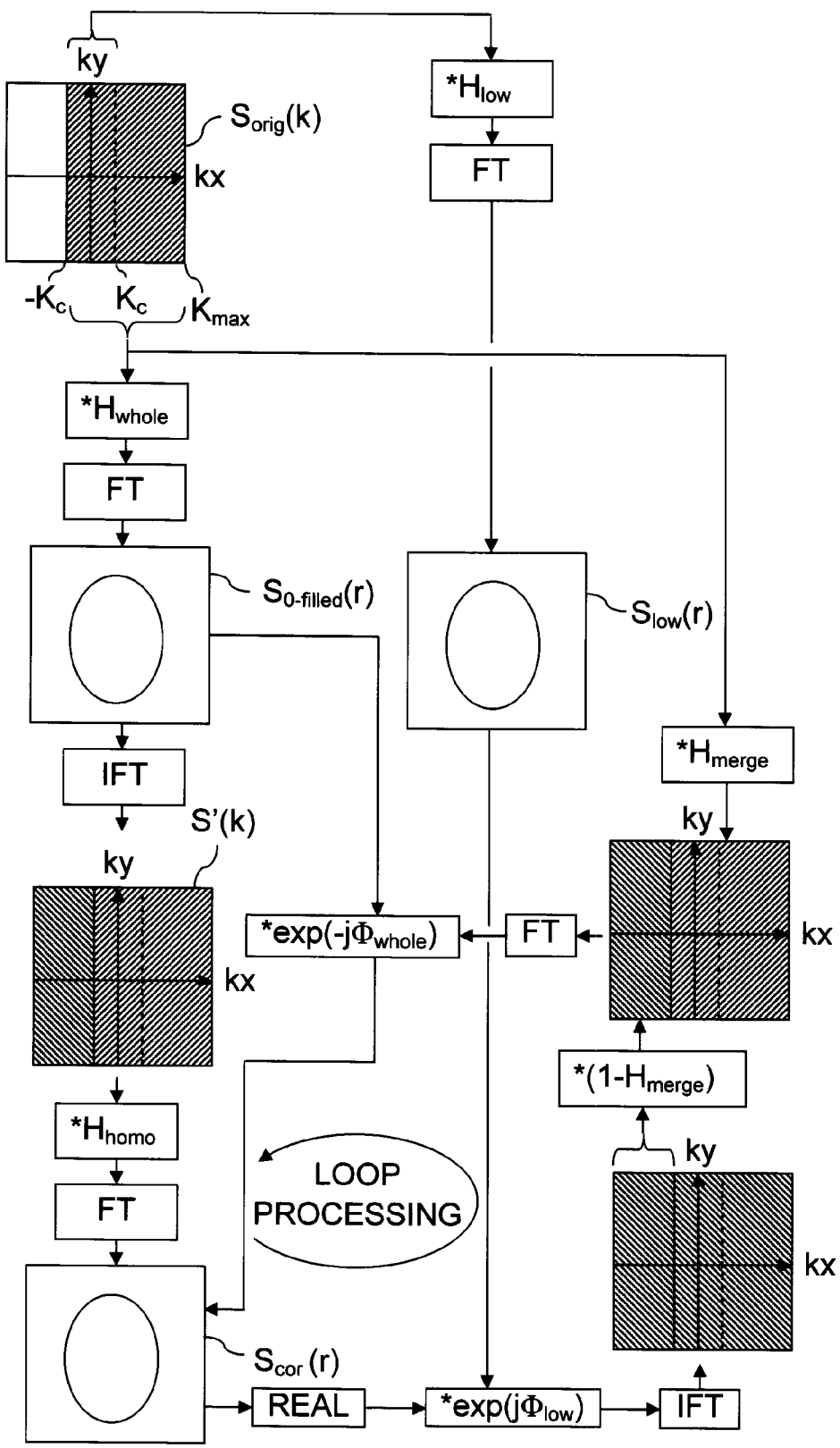
FIG. 10 is a chart explaining a method of AFI processing in a case of performing loop processing, which reduces a phase error, following the data processing shown in FIG. 3.

FIG. 10 is a chart explaining a method of AFI processing in a case of performing loop processing, which reduces a phase error, following the data processing shown in FIG. 3.

The loop processing can be configured by the following series of processing. First, the real part extraction processing which takes the real parts of the real space data is performed to the MR image data $S_{cor}(r)$. Next, processing for shifting the phases of the real parts after the real part extraction processing, in the direction opposite to the direction of the phase correction is performed. Next, processing for replacing the data, corresponding to the sampling region ($-K_c \leq k \leq K_{max}$) among the k-space data obtained by the IFT of the real space data after the processing for shifting the phases of the real parts in the opposite direction to the direction of the phase correction, with the MR data $S_{orig}(k)$ in the sampling region is performed. Next, processing for obtaining updated MR image data by the FT of the replaced k-space data into real space data and shifting the phases of the real space data in the direction of the phase correction is performed. This loop processing can be performed once or several times. In case of performing the loop processing several times, the loop processing becomes the convergence calculation which approximates the imaginary parts of the MR image data $S_{cor}(r)$ to zero.

Note that, it has been confirmed that the image quality can be improved by performing the inverse phase correction processing, which shifts the phases of real parts in the opposite direction to the direction of phase correction, using the phase distribution $\Phi_{low}$ in the region in the low frequency side consisting of the symmetric sampling part among the sampling region and performing the phase correction processing, which shifts the phases in the direction of phase correction, using the phase distribution $\Phi_{whole}$ corresponding to the sampling region, as exemplified in FIG. 10. Therefore, the inverse phase correction processing is processing which multiplies real space data by $\exp(j\Phi_{low})$ while the phase correction processing is processing which multiplies real space data by $\exp(j\Phi_{whole})$.

The phase distribution $\Phi_{low}$ in the low frequency region can be obtained based on the real space data $S_{low}(r)$ obtained by transforming the MR data $S_{orig}(k)$ in the region in the low frequency side. Specifically, the real space data $S_{low}(r)$ corresponding to the symmetric part in the low frequency region can be generated by multiplying the window function $H_{low}(k)$ with the MR data $S_{orig}(k)$ to extract the symmetric part and the FT of the extracted symmetric part. Then, the phase distribution $\Phi_{low}$ in the low frequency region can be calculated by the formula (7).

$$\exp\{-j\Phi_{low}(x)\}=S_{low}*(r)/|S_{low}(r)| \quad (7)$$

wherein * in the formula (7) represents complex conjugate.

Similarly, the phase distribution $\Phi_{whole}$ corresponding to the sampling region also can be obtained based on the real space data obtained by transforming the MR data $S_{orig}(k)$ in the sampling region. Specifically, the amplitude image data $S_{0\text{-}filled}(r)$ can be generated by multiplying the window function $H_{whole}(k)$ for the 0-filling with the MR data $S_{orig}(k)$ to extract the data in the sampling region and the FT of the extracted data. Then, the phase distribution $\Phi_{whole}$ in the sampling region can be calculated by the formula (8).

$$\exp\{-j\Phi_{whole}(x)\}=S_{0\text{-}filled}*(r)/|S_{0\text{-}filled}(r)| \quad (8)$$

wherein * in the formula (8) represents complex conjugate.

The processing which replaces the data corresponding to the sampling region, among the k-space data obtained by the IFT of the real space data after the inverse phase correction processing, with the MR data $S_{orig}(k)$ in the sampling region can be performed by an operation using a data extraction function $H_{merge}(k)$ for extracting the data in the sampling region. Specifically, the replacing processing can be performed by processing to add the k-space data, extracted by multiplying the MR data $S_{orig}(k)$ by the data extraction function $H_{merge}(k)$, to the k-space data extracted by multiplying the k-space data, obtained by the IFT of the real space data after the inverse phase correction processing, by the function $\{1-H_{merge}(k)\}$.

Next, an operation and an action of the magnetic resonance imaging apparatus 20 will be described.

First, the object P is set to the bed 37 beforehand, and a static magnetic field is generated at an imaging area in the magnet 21 for static magnetic field, excited by the static-magnetic-field power supply 26. Further, the shim-coil power supply 28 supplies a predetermined current to the shim coil 22 based on data acquired by a pre-scan for shimming, thereby uniformizing the static magnetic field generated at the imaging area.

Then, the sequence controller 31 drives the gradient power supply 27, the transmitter 29, and the receiver 30 in accordance with the pulse sequence for AFI set in the imaging condition setting part 40, thereby generating a gradient magnetic field at the imaging area having the set object P, and further generating RF signals from the RF coil 24.

Consequently, the RF coil 24 receives MR signals generated due to the magnetic resonance in the object P. Then, the receiver 30 receives the MR signals from the RF coil 24 and generates raw data, which are digital data of the MR signals. The receiver 30 supplies the generated raw data to the sequence controller 31. The sequence controller 31 supplies the raw data to the data processing part 41. The data processing part 41 arranges the raw data in the k-space formed in the k-space database 43.

Note that, the raw data arranged in the k-space are acquired by the imaging conditions for the AFI. Therefore, the raw data becomes MR data $S_{orig}(k)$ in an asymmetric sampling region $-K_c \leq k \leq K_{max}$.

Next, the data processing part 41 generates MR image data by image reconstruction processing including the FT of the k-space data acquired from the k-space. Specifically, the AFI processing part 41A performs the AFI processing without the phase correction processing as shown in FIG. 3 or FIG. 9. Alternatively, the AFI processing of which post processing is the loop processing including the phase correction processing shown in FIG. 10 is performed in the AFI processing part 41A. Consequently, the MR image data $S_{cor}(r)$ approximately similar to the MR image data generated from the k-space data sampled symmetrically can be generated in a short data processing time.

Then, after the required image processing of the MR image data $S_{cor}(r)$ in the data processing part 41, the MR image data $S_{cor}(r)$ can be displayed on the display unit 34 or stored in the image database 44.

That is, the magnetic resonance imaging apparatus 20 mentioned above is an apparatus configured to treat the amplitude image data $S_{0\text{-}filled}(r)$, obtained by the 0-filling of asymmetric MR data acquired according to imaging conditions for AFI, as data after the phase correction in the conventional MoFIR method.

Therefore, according to the magnetic resonance imaging apparatus 20, the phase correction processing which has been required conventionally in the AFI processing becomes unnecessary. Moreover, it is possible to generate MR image data, having an image quality similar to the image quality in the MoFIR method, without acquiring raw data or complex image data for the phase correction since the phase correction processing is unnecessary. In addition, the image reconstruction processing time can be shortened by the calculation time conventionally required for the phase correction. That is, in the magnetic resonance imaging apparatus 20, it is possible to reconstruct image data fast with keeping an accuracy similar to that in the MoFIR method.

Figure 11:
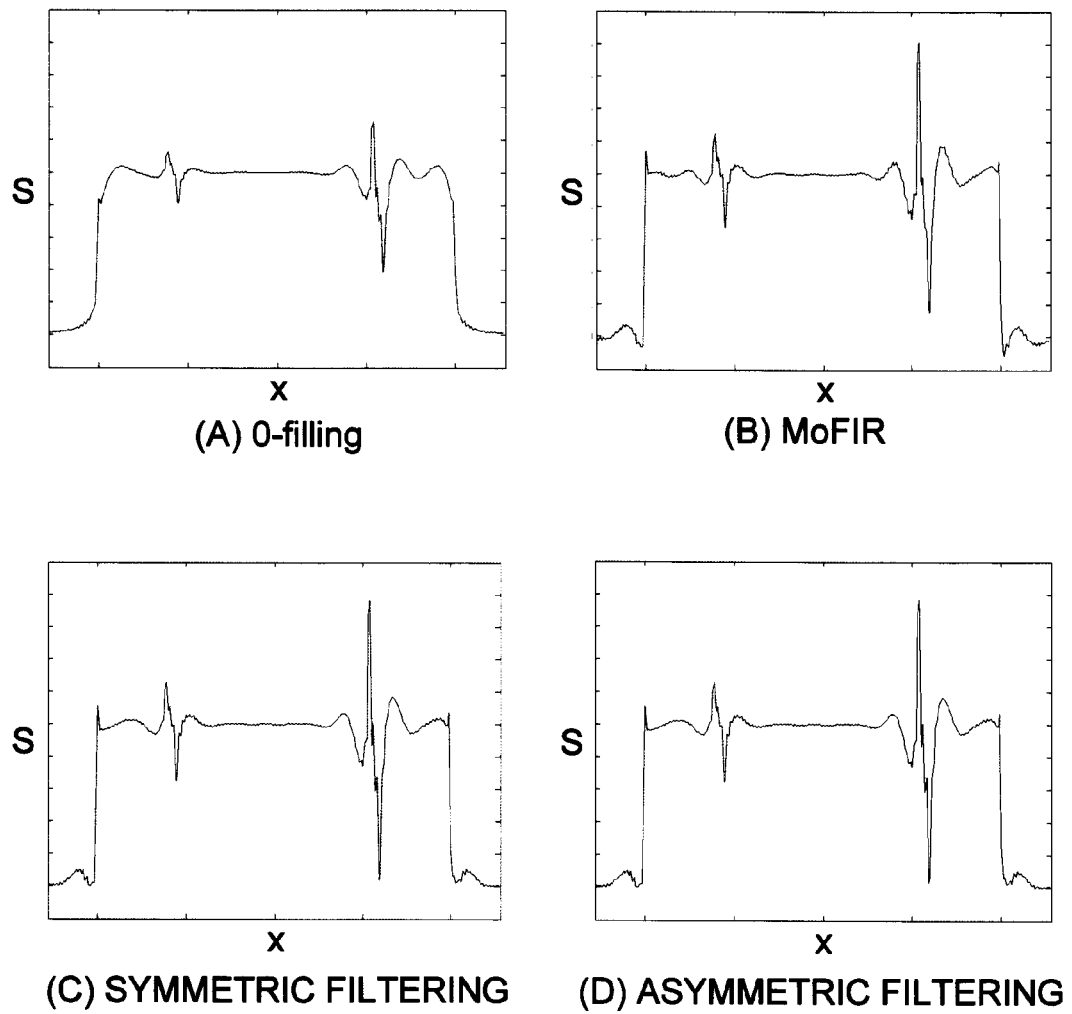
FIG. 11 shows graphs for comparing 1D simulation data generated by the AFI processing shown in FIG. 3 with those by the conventional AFI processing.

FIG. 11 shows graphs for comparing 1D simulation data generated by the AFI processing shown in FIG. 3 with those by the conventional AFI processing.

In FIG. 11, each horizontal axis represents positions x in a one axis direction and each vertical axis represents relative image signal intensities S at the positions x. Moreover, FIG. 11(A) is simulation data obtained by performing only the 0-filling of asymmetric k-space data, FIG. 11(B) is simulation data reconstructed from the asymmetric k-space data by the conventional MoFIR method, FIG. 11(C) is simulation data reconstructed from the asymmetric k-space data using a symmetric window function $H_{high\_sym}(k)$ in the procedure shown in FIG. 3 and FIG. 11(D) is simulation data reconstructed from the asymmetric k-space data using an asymmetric window function $H_{high\_asym}(k)$ in the procedure shown in FIG. 3.

According to FIG. 11, it can be confirmed that blurs in each of the simulation data sets, shown in (C) and (D), each reconstructed by the AFI processing method of the present invention are more improved than those in the simulation data, shown in (A), obtained by performing only the 0-filling. Moreover, when (B), (C) and (D) of FIG. 11 are referred to, it can be confirmed that data which are not inferior especially compared with the simulation data reconstructed by the MoFIR method are obtained by the AFI processing method of the present invention regardless of using the symmetric window function $H_{high\_sym}(k)$ or the asymmetric window function $H_{high\_asym}(k)$.

Furthermore, it can be confirmed by the 1D simulation that the root mean square error (RMSE) becomes small by performing the loop processing, which reduces the phase error, as shown in FIG. 10, compared with the case without performing the loop processing.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

For example, an example of sampling k-space data asymmetric only in the kx direction in a 2D k-space (kx, ky) having the kx axis and the ky axis has been mainly described in the above mentioned embodiment. However, the AFI processing without the phase correction processing can be performed by a similar way also in a case of sampling k-space data asymmetric in one direction or the two directions out of the kx direction and the ky direction. Furthermore, the AFI processing without the phase correction processing can be performed by a similar way also in a case of sampling k-space data asymmetric in one direction, two directions, or the three directions in a 3D k-space (kx, ky, kz) having the kx axis, the ky axis and the kz axis.

When sampling is performed asymmetrically in not less than two directions, a not less than 2D window function can be generated by generating a 1D window function for each of the plural asymmetric sampling directions and multiplying the generated 1D window functions by each other. More specifically, what is necessary is to generate a 1D window function $H_{whole}(k)$ for the 0-filling and a window function $H_{homo}(k)$ for correcting the degradation in the high frequency components, for each of the kx axis direction, the ky axis direction and the kz axis direction, and to multiply the generated window functions by each other between the directions, as shown by the formula (9-1) and the formula (9-2).

$$H_{whole}(kx,ky,kz)=H_{whole}(kx)*H_{whole}(ky)*H_{whole}(kz) \quad (9\text{-}1)$$

$$H_{homo}(kx,ky,kz)=H_{homo}(kx)*H_{homo}(ky)*H_{homo}(kz) \quad (9\text{-}2)$$

In this case, the FT and the IFT which are first performed in the AFI processing are performed as 1D, 2D or 3D transformations according to asymmetric sampling directions. On the other hand, the last FT is performed in all the directions. Thereby, image data after the AFI processing can be obtained.

What is claimed is:

1. A magnetic resonance imaging (MRI) apparatus comprising:
    MRI system components including static and gradient magnetic field generators, radio frequency (RF) transmitter and receiver circuits, at least one RF coil and at least one processor connected to control said components as to
    acquire first magnetic resonance k-space data from an object, the magnetic resonance data corresponding to a sampling region asymmetric in a wave number direction in k-space;
    generate first amplitude image data, in real space, based on first k-space data after zero padding to a non-sampled region of the magnetic resonance data and without phase correction of the first k-space data, said zero padding being performed by applying an $H_{low}(k)$ window function which defines a symmetrical portion of the acquired magnetic resonance data in a low frequency region from the acquired asymmetric MR data, where zero padding is performed outside the $H_{low}(k)$ window function region;
    generate second magnetic resonance k-space image data, based on the first amplitude image data, by (a) transform data processing of the amplitude image data or (b) convolution processing of the amplitude image data, wherein phase components of the generated second k-space image data simulate phase-corrected MoFIR (modified finite impulse response) k-space data;

in response to transform data processing of the amplitude image data being performed, perform filtering of the second k-space data by a window function $H_{homo}(k)$ and then converting the filtered second k-space data into second real space image data with reduced deterioration in high frequency components simulating real space image data generated by MoFIR, or in response to convolution processing of the amplitude image data being used, employing a filter function in real space derived by converting said window function $H_{homo}(k)$ to produce second real space image data with reduced deterioration in high frequency components simulating real space image data generated by MoFIR, wherein the window function $H_{homo}(k)$ has a gain in a high frequency region and again in a low frequency region, the gain in the high frequency region being larger than the gain in the low frequency region, the high frequency region consisting of the non-sampled region and an asymmetrically sampled portion out of the asymmetrically sampled region, the low frequency region being a symmetrically sampled portion out of the asymmetrically sampled region.

2. The magnetic resonance imaging apparatus of claim 1, wherein the gain in the high frequency region of the filter function $H_{homo}(k)$ is not more than twice the gain in the low frequency region.

3. The magnetic resonance imaging apparatus of claim 1, wherein the window function $H_{homo}(k)$ is a smoothly varying function.

4. A magnetic resonance imaging apparatus comprising:
MRI system components including static and gradient magnetic field generators, radio frequency (RF) transmitter and receiver circuits, at least one RF coil and at least one processor connected to control said components as to acquire first magnetic resonance k-space data from an object, the magnetic resonance data corresponding to a sampling region asymmetric in a wave number direction in k-space;

generate first amplitude image data, in real space, based on first k-space data after zero padding to a non-sampled region of the magnetic resonance data and without phase correction of the first k-space data, said zero padding being performed by applying an $H_{low}(k)$ window function which defines a symmetrical portion of the acquired magnetic resonance data in a low frequency region from the acquired asymmetric MR data, where zero padding is performed outside the $H_{low}(k)$ window function region;

generate second magnetic resonance k-space image data by (a) transform data processing of the amplitude image data or (b) convolution processing of the amplitude image data, wherein phase components of the generated second k-space image data simulate phase-corrected MoFIR (modified finite impulse response) k-space data; and in response to transform data processing of the amplitude image data being performed, perform filtering of the second k-space data by a window function $H_{homo}(k)$ and then converting the filtered second k-space data into second real space image data with reduced deterioration in high frequency components simulating real space image data generated by MoFIR, or in response to convolution processing of the amplitude image data being performed, employing a function in real space derived by converting said window function $H_{homo}(k)$ to produce second real space image data with reduced deterioration in high frequency components simulating real space image data generated by MoFIR, wherein the window function $H_{homo}(k)$ has a gain in a high frequency region and again in a low frequency region, the gain in the high frequency region being larger than the gain in the low frequency region, the high frequency region being an asymmetrically sampled portion out of the asymmetrically sampled region, the low frequency region being a symmetrically sampled portion out of the asymmetrically sampled region.

5. The magnetic resonance imaging apparatus of claim 4, wherein the gain of filter function $H_{homo}(k)$ in the high frequency region is not less than twice the gain in the low frequency region and not more than four times the gain in the low frequency region, and a gain in the non-sampling region is zero.

6. A magnetic resonance imaging apparatus comprising:
MRI system components including static and gradient magnetic field generators, radio frequency (RF) transmitter and receiver circuits, at least one RF coil and at least one processor connected to control said components as to acquire first magnetic resonance k-space data from an object, the magnetic resonance data corresponding to a sampling region asymmetric in a wave number direction in k-space;

generate first amplitude image data, in real space, based on first k-space data after zero padding to a non-sampled region of the magnetic resonance data and without phase correction of the first k-space data, said zero padding being performed by applying an $H_{low}(k)$ window function which defines a symmetrical portion of the acquired magnetic resonance data in a low frequency region from the acquired asymmetric MR data, where zero padding is performed outside the $H_{low}(k)$ window function region;

generate second magnetic resonance k-space image data by (a) transform data processing of the amplitude image data or (b) convolution processing of the amplitude image data, wherein phase components of the generated second k-space image data simulate phase-corrected MoFIR (modified finite impulse response) k-space data; and in response to transform data processing of the amplitude image data being performed, perform filtering of the second k-space data by a window function $H_{homo}(k)$ and then converting the filtered second k-space data into second real space image data with reduced deterioration in high frequency components simulating real space image data generated by MoFIR, or in response to convolution processing of the amplitude image data being performed, employing a filter function in real space derived by converting said window function $H_{homo}(k)$ to produce second real space image data with reduced deterioration in high frequency components simulating real space image data generated by MoFIR, wherein said at least one computer is configured to perform a series of processing one time or plural times, the series including first processing, second processing, third processing, fourth processing, fifth processing, and sixth processing, the first processing being performed for the magnetic resonance image data and extracting a real part of real space data, the second processing shifting a phase of the real part in a direction opposite to a phase correction direction, the third processing converting real space data after the second processing to k-space data, the fourth processing replacing a part of the k-space data derived by the third processing, the part corresponding to the sampled region, being replaced with magnetic resonance data in the sampled region, the fifth processing converting k-space data derived by the fourth processing to real space data, and the sixth processing shifting a phase of the real space data derived by the fifth processing in the phase correction direction to generate updated magnetic resonance image data.

7. The magnetic resonance imaging apparatus of claim 6, wherein the second processing is performed using a phase distribution in a low frequency region and the sixth processing using a phase distribution corresponding to the sampling region, the low frequency region being a symmetrically sampled portion out of the asymmetrically sampled region, the phase distribution in the low frequency region being derived based on real space data derived by converting magnetic resonance data in the low frequency region out of the magnetic resonance data in the asymmetrically sampled region, and the phase distribution corresponding to the sampled region being derived based on real space data derived by converting the magnetic resonance data in the asymmetrically sampled region.

8. A magnetic resonance imaging (MRI) method comprising:

acquiring first magnetic resonance k-space data from an object, the magnetic resonance data corresponding to a sampling region asymmetric in a wave number direction in k-space;

generating first amplitude image data, in real space, based on first k-space data after zero padding to a non-sampled region of the magnetic resonance data and without phase correction of the first k-space data, said zero padding being performed by applying an $H_{low}(k)$ window function which defines a symmetrical portion of the acquired magnetic resonance data in a low frequency region from the acquired asymmetric MR data, where zero padding is performed outside the $H_{low}(k)$ window function region;

generating second magnetic resonance k-space image data by (a) transform data processing of the amplitude image data or (b) convolution processing of the amplitude image data, wherein phase components of the generated second k-space image data simulate phase-corrected MoFIR (modified finite impulse response) k-space data; and in response to transform data processing of the amplitude image data being performed, filtering the second k-space data by a window function $H_{homo}(k)$ and then converting the filtered second k-space data into second real space image data with reduced deterioration in high frequency components simulating real space image data generated by MoFIR, or in response to convolution processing of the amplitude image data being performed, employing a filter function in real space derived by converting said window function $H_{homo}(k)$ to produce second real space image data with reduced deterioration in high frequency components simulating real space image data generated by MoFIR, wherein the window function $H_{homo}(k)$ has a gain in a high frequency region and again in a low frequency region, the gain in the high frequency region being larger than the gain in the low frequency region, the high frequency region consisting of the non-sampled region and an asymmetrically sampled portion out of the asymmetrically sampled region, the low frequency region being a symmetrically sampled portion out of the asymmetrically sampled region.

9. The magnetic resonance imaging method of claim 8, wherein the gain of said filter function $H_{homo}(k)$ in the high frequency region is not more than twice the gain in the low frequency region.

10. The magnetic resonance imaging method of claim 8, wherein the window function $H_{homo}(k)$ is a smoothly varying function.

11. A magnetic resonance imaging method comprising:

acquiring first magnetic resonance k-space data from an object, the magnetic resonance data corresponding to a sampling region asymmetric in a wave number direction in k-space;

generating first amplitude image data, in real space, based on first k-space data after zero padding to a non-sampled region of the magnetic resonance data and without phase correction of the first k-space data, said zero padding being performed by applying an $H_{low}(k)$ window function which defines a symmetrical portion of the acquired magnetic resonance data in a low frequency region from the acquired asymmetric MR data, where zero padding is performed outside the $H_{low}(k)$ window function region;

generating second magnetic resonance k-space image data by (a) transform data processing of the amplitude image data or (b) convolution processing of the amplitude image data, wherein phase components of the generated second k-space image data simulate phase-corrected MoFIR (modified finite impulse response) k-space data; and in response to transform data processing of the amplitude image data being performed, filtering the second k-space data by a window function $H_{homo}(k)$ and then converting the filtered second k-space data into second real space image data with reduced deterioration in high frequency components simulating real space image data generated by MoFIR, or in response to convolution processing of the amplitude image data being performed, employing a filter function in real space derived by converting said window function $H_{homo}(k)$ to produce second real space image data with reduced deterioration in high frequency components simulating real space image data generated by MoFIR, wherein the window function $H_{homo}(k)$ has a gain in a high frequency region and again in a low frequency region, the gain in the high frequency region being larger than the gain in the low frequency region, the high frequency region being an asymmetrically sampled portion out of the asymmetrically sampled region, the low frequency region being a symmetrically sampled portion out of the asymmetrically sampled region.

12. The magnetic resonance imaging method of claim 11, wherein the gain of said filter function $H_{homo}(k)$ in the high frequency region is not less than twice the gain in the low frequency region and not more than four times the gain in the low frequency region, and a gain in the non-sampling region is zero.

13. A magnetic resonance imaging apparatus comprising:
acquiring first magnetic resonance k-space data from an object, the magnetic resonance data corresponding to a sampling region asymmetric in a wave number direction in k-space;
generating first amplitude image data, in real space, based on first k-space data after zero padding to a non-sampled region of the magnetic resonance data and without phase correction of the first k-space data, said zero padding being performed by applying an $H_{low}(k)$ window function which defines a symmetrical portion of the acquired magnetic resonance data in a low frequency region from the acquired asymmetric MR data, where zero padding is performed outside the $H_{low}(k)$ window function region;
generating second magnetic resonance k-space image data by (a) transform data processing of the amplitude image data or (b) convolution processing of the amplitude image data, wherein phase components of the generated second k-space image data simulate phase-corrected MoFIR (modified finite impulse response) k-space data; and
in response to transform data processing of the amplitude image data being performed, filtering the second k-space data by a window function $H_{homo}(k)$ and then converting the filtered second k-space data into second real space image data with reduced deterioration in high frequency components simulating real space image data generated by MoFIR, or
in response to convolution processing of the amplitude image data being performed, employing a filter function in real space derived by converting said window function $H_{homo}(k)$ to produce second real space image data with reduced deterioration in high frequency components simulating real space image data generated by MoFIR,
wherein said at least one computer is configured to perform a series of processing one time or plural times, the series including first processing, second processing, third processing, fourth processing, fifth processing, and sixth processing,
the first processing being performed for the magnetic resonance image data and extracting a real part of real space data,
the second processing shifting a phase of the real part in a direction opposite to a phase correction direction,
the third processing converting real space data after the second processing to k-space data,
the fourth processing replacing a part of the k-space data derived by the third processing, the part corresponding to the sampled region, being replaced with magnetic resonance data in the sampled region,
the fifth processing converting k-space data derived by the fourth processing to real space data, and
the sixth processing shifting a phase of the real space data derived by the fifth processing in the phase correction direction to generate updated magnetic resonance image data.

14. The magnetic resonance imaging method of claim 13, wherein
the second processing is performed using a phase distribution in a low frequency region and the sixth processing using a phase distribution corresponding to the sampling region,
the low frequency region being a symmetrically sampled portion out of the asymmetrically sampled region,
the phase distribution in the low frequency region being derived based on real space data derived by converting magnetic resonance data in the low frequency region out of the magnetic resonance data in the asymmetrically sampled region, and
the phase distribution corresponding to the sampled region being derived based on real space data derived by converting the magnetic resonance data in the asymmetrically sampled region.

* * * * *